United States Patent
Su (10) Patent No.: US 9,250,170 B2
(45) Date of Patent: Feb. 2, 2016

(54) TORQUE TESTING MACHINE WITH DOUBLE DRIVE DEVICES

(71) Applicant: Hong Ann Tool Industries Co., Ltd., Taichung (TW)

(72) Inventor: Cheng-Wei Su, Taichung (TW)

(73) Assignee: Hong Ann Tool Industries Co., Ltd., Taichung (TW)

( * ) Notice: Subject to any disclaimer, the term of this patent is extended or adjusted under 35 U.S.C. 154(b) by 30 days.

(21) Appl. No.: 14/320,689

(22) Filed: Jul. 1, 2014

(65) Prior Publication Data
US 2015/0059490 A1 Mar. 5, 2015

(30) Foreign Application Priority Data

Aug. 29, 2013 (TW) .............................. 102131002 A (51) Int. Cl.
*G01N 3/22* (2006.01)

(52) U.S. Cl.
CPC ........................................ *G01N 3/22* (2013.01)

(58) Field of Classification Search
USPC .......................... 73/862.08, 1.12, 862.23, 847
See application file for complete search history.

(56) References Cited

U.S. PATENT DOCUMENTS

| 5,181,425 | A | * | 1/1993 | Livingston | ............ G01L 25/003 73/1.11 |
| 5,703,277 | A | * | 12/1997 | Grabovac | ............. G01L 25/003 73/1.09 |
| 8,117,887 | B2 | * | 2/2012 | Schwafertz | ........... G01L 25/003 73/1.01 |
| 8,453,519 | B2 | * | 6/2013 | Zhang | ................... G01L 5/0042 73/862.08 |

FOREIGN PATENT DOCUMENTS

TW M345232 U 11/2008

* cited by examiner

*Primary Examiner* — Jewel V Thompson
(74) *Attorney, Agent, or Firm* — Alan D. Kamrath; Kamrath IP Lawfirm, P.A.

(57) ABSTRACT

A torque testing machine includes a testing head and a calculating device connecting to the testing head to calculate a torque transmitted to the testing head. A first drive device includes a first connecting head being cooperative with the testing head. The first connecting head and the testing head oppose to each other. The first connecting head is rotatable about an axis. A second drive device includes a second connecting head being cooperative with the testing head. The second connecting head offsets a distance from the axis and is movable tangentially to the distance.

15 Claims, 13 Drawing Sheets

TORQUE TESTING MACHINE WITH DOUBLE DRIVE DEVICES

BACKGROUND OF THE INVENTION

1. Field of the Invention

The present invention relates to a torque testing machine and, particularly, to a torque testing machine including at least two drive devices.

2. Description of the Related Art

TW Patent No. M345232 shows a torque testing machine including a testing head, a connecting head and two holding members. The testing head and the connecting head are aligned and opposite to each other. The testing head is rotatable about an axis, and the testing head and the connecting head face each other in the direction of the axis. Each of the two holding members has various height positions. Each of the two holding members is mounted on a rail. Each of the two holding members is movable along the rail engaged therewith. Each of the two holding members is used to hold an end of an object to be tested, and the testing head is used to hold another end of the object. The testing head can rotate the object to be tested and measure a torque force the object withstands. Alternatively, the connecting head is used to hold the object to be tested. However, types of objects to be tested by the torque testing machine are limited.

The present invention is, therefore, intended to obviate or at least alleviate the problems encountered in the prior art.

SUMMARY OF THE INVENTION

According to the present invention, a torque testing machine includes a testing head and a calculating device connecting to the testing head to calculate a torque transmitted to the testing head. A first drive device includes a first connecting head being cooperative with the testing head. The first connecting head and the testing head oppose to each other. The first connecting head is rotatable about an axis. A second drive device includes a second connecting head being cooperative with the testing head. The second connecting head offsets a distance from the axis and is movable tangentially to the distance.

When a first object to be tested is driven by the first drive device, the first connecting head is in a rotational motion about the axis and creates a first torque transmitted to the testing head.

When a second object to be tested is driven by the second drive device, the second connecting head is in a motion tangential to the distance and creates a second torque transmitted to the testing head.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure. The abstract is neither intended to define the invention, which is measured by the claims, nor is it intended to be limiting as to the scope of the invention in any way.

It is therefore an objective of the present invention to provide a torque testing machine including at least two drive devices.

It is another objective of the present invention to provide a torque testing machine that can test various types of objects.

Other objectives, advantages, and new features of the present invention will become apparent from the following detailed description of the invention when considered in conjunction with the accompanied drawings.

DETAILED DESCRIPTION OF THE INVENTION

FIGS. 1 through 13 show a torque testing machine 10 in accordance with the present invention. The torque testing machine 10 includes a testing head 11 and a calculating device 22 connecting to the testing head 11 to calculate a torque transmitted to the testing head 11. The calculating device 12 is disposed adjacent to the testing head 11. The calculating device 12 has an end connecting to the testing head 11.

A first drive device 20 includes a first connecting head 21 being cooperative with the testing head 11. The first connecting head 21 and the testing head 11 disposed opposite to each other. The first connecting head 21 is rotatable about a first axis L1.

The testing head 11 is movable to various positions in a direction of a second axis L2. The first and second axes L1 and L2 are aligned with each other. The calculating device 12 connects to the testing head 11 such that the calculating device 12 moves with the testing head 11. A feed control 13 is used to operatively move the testing head 11. The feed control 13 has an end connecting to the calculating device 12, and the calculating device 12 connects to the testing head 11. The testing head 11 is disposed on at least one track 24. The at least one track 24 extends in the direction of the second axis L2. In the embodiment, there are three tracks 24. The three tracks 24 are evenly distributed.

The first connecting head 21 and the testing head 11 face each other in the direction of the second axis L2. The first connecting head 21 separates from the testing head 11 in the direction of the second axis L2. The testing head 11 can move close to or away from the first connecting head 21.

Figure 1:
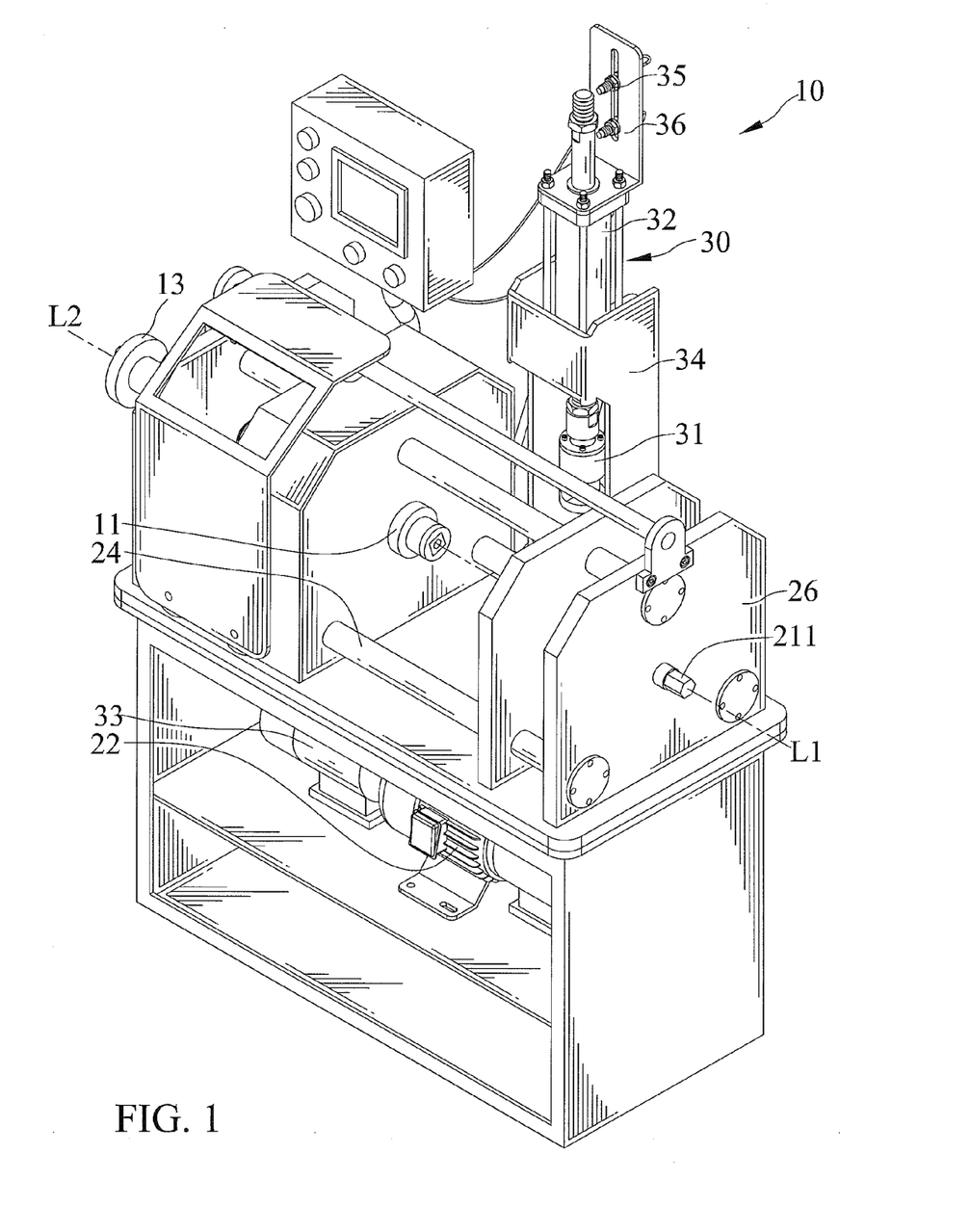
FIG. 1 is a perspective view of a torque testing machine in accordance with the present invention.
Figure 2:
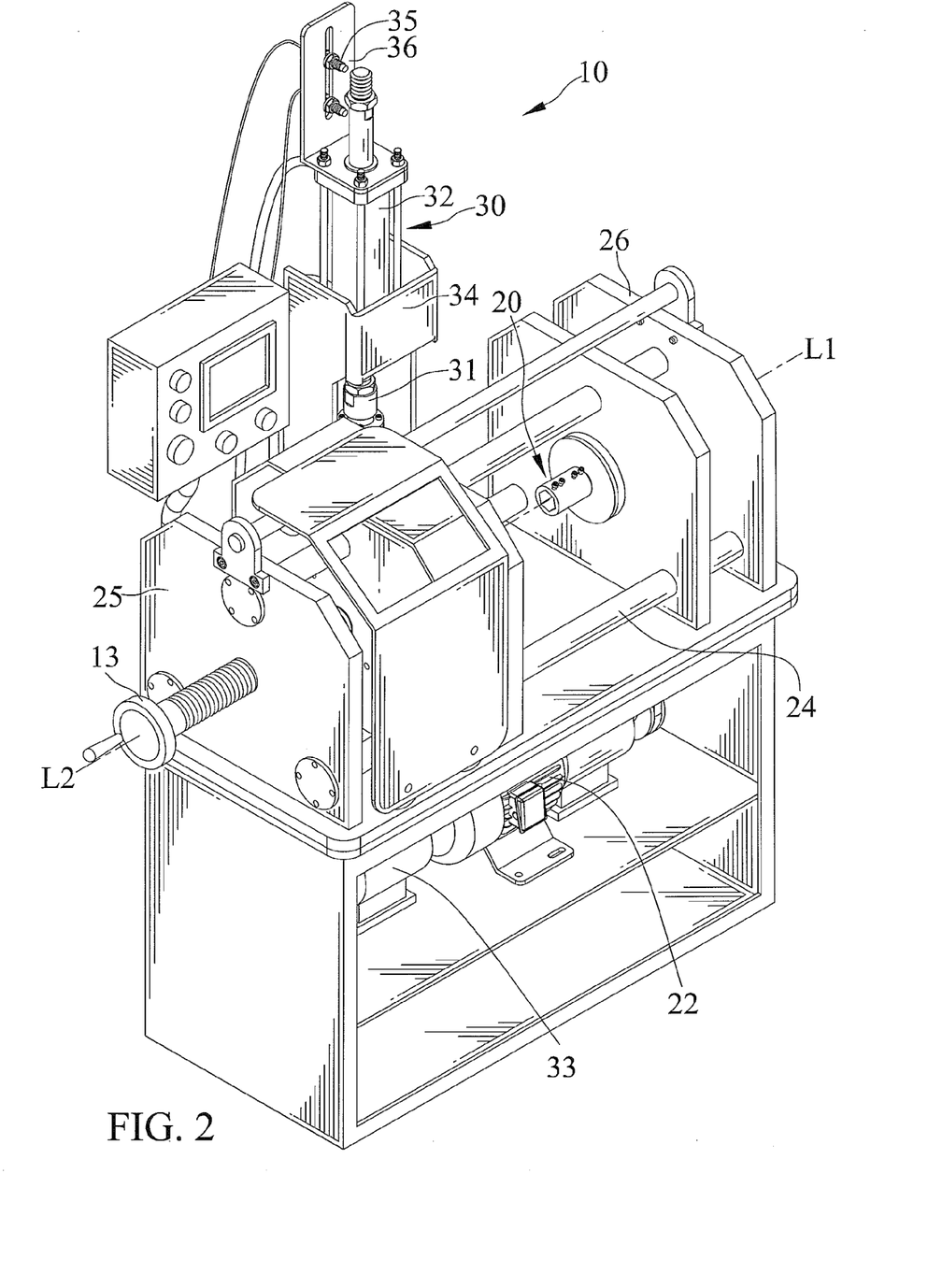
FIG. 2 is a perspective view of the torque testing machine in an angle different from FIG. 1.
Figure 3:
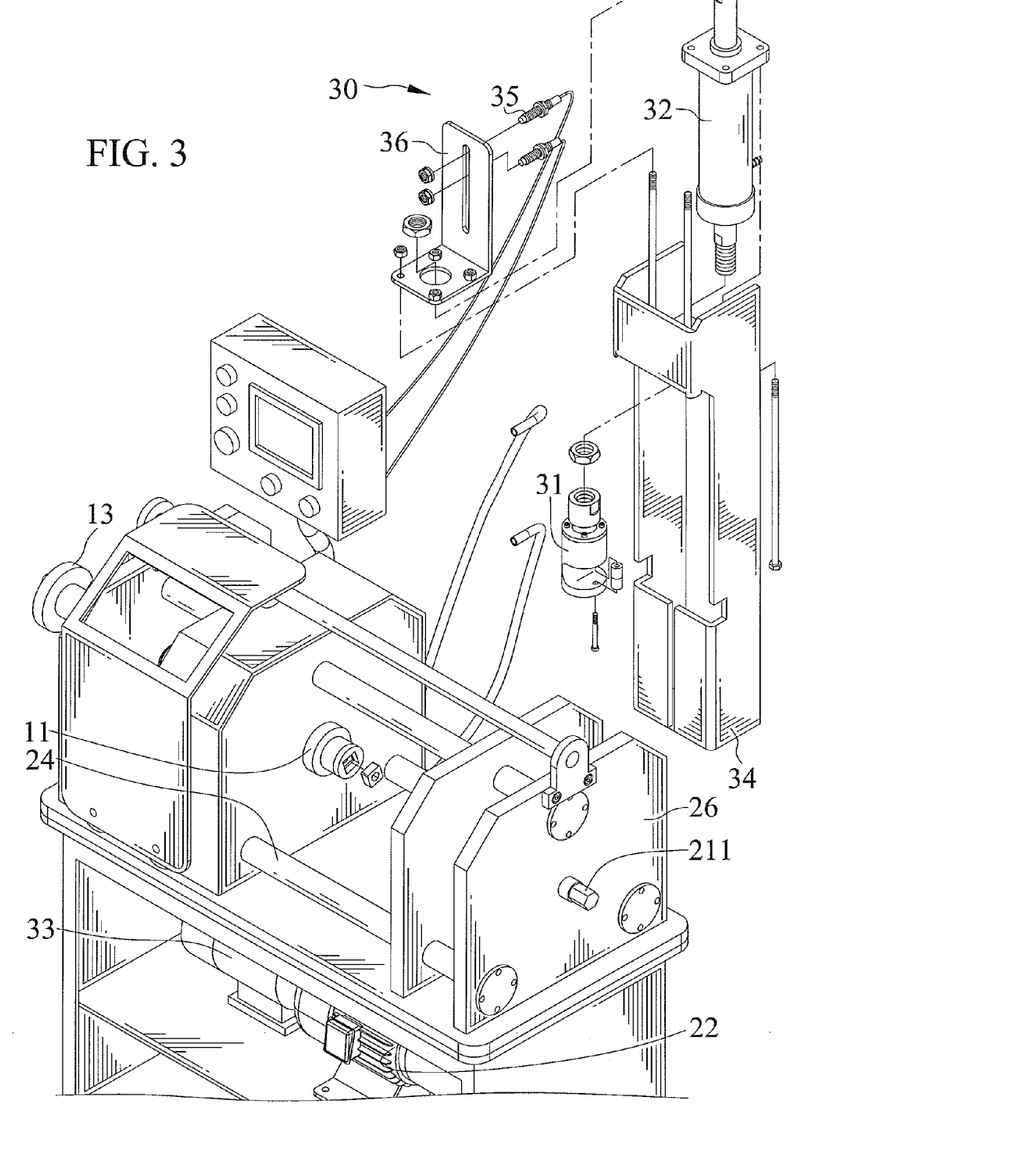
FIG. 3 is an exploded perspective view of the torque testing machine of the present invention.
Figure 4:
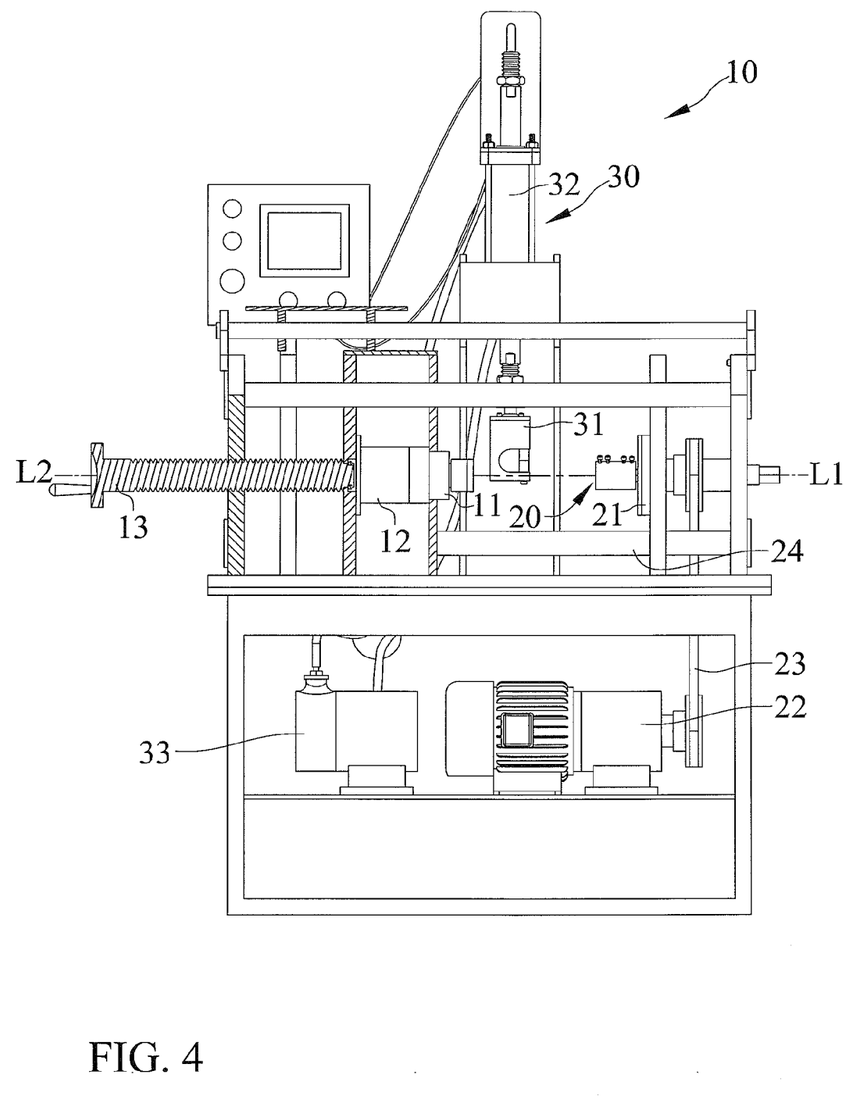
FIG. 4 is a cross-sectional view of the torque testing machine of the present invention.

The first connecting head 21 includes a control input 211 extending therefrom and rotating therewith, and wherein the control input is operatively rotatable to cause the first connecting head in a rotational motion.

The torque testing machine 10 includes a first seat 25 and a second seat 26 separating from the first seat 25 in the direction of the second axis L2. The testing head 11 is disposed between the first and second seats 25 and 26. The testing head 11 is disposed closer to the first seat 25. The first seat 25 supports the feed control 13. The first and second seats 25 and 26 include the at least one track 24 extending therebetween.

The first connecting head 21 is disposed between the first and second seats 25 and 26. The first connecting head 21 and the control input 211 are disposed on opposite sides of the second seat 26. The control input 211 protrudes outside a space delimited between the first and second seats 25 and 26. The control input 211 has a polygonal end. In the embodiment, the control input has a hexagonal end, which includes an outer periphery of a hexagonal shape. The first connecting head 21 can be operatively turned by turning the polygonal end of the control input 211. A tool can be used to easily turn the control input 211, with the tool engaging with the polygonal end of the control input 211.

The first power source 22 is an electric motor, but not limiting. The first transmission mechanism includes an axle which defines an output axle of the first power source 22. The first power source 22 in operation includes the axle in a rotational motion. The power source 22 is offset from the first connecting head 21. The power source 22 is disposed below the first connecting head 21 in a direction transverse to the direction of the first axis L1. Thus, the axle is offset from the first axis L1. The first transmission mechanism further includes a drive belt 23. The drive belt 23 is routed on the axle and the first connecting head 21. Thus, the axle in a rotational motion turns the first connecting head 21 through the drive belt 23.

A second drive device 30 includes a second connecting head 31 being cooperative with the testing head 11. The second connecting head 31 offsets a distance D from the first axis L1 and is movable tangentially to the distance D. The second connecting head 31 can move tangentially to an imaginary circle centered on the first axis L1. Thus, the first axis L1 pass through the center of the imaginary circle. The second drive device 30 is disposed between the first and second seats 25 and 26.

A first power source 22 drives a first transmission mechanism to turn the first connecting head 21 and a second power source 33 to drive a second transmission mechanism to move the second connecting head 31, respectively. The first drive transmission mechanism interconnects the first power source 22 and the first connecting head 21 and the second transmission mechanism interconnects the second power source 33 and the second connecting head 31, respectively. The second connecting head 31 is reciprocally movable. The second transmission mechanism includes a driver 32 with a shaft being reciprocally movable and connecting to the second connecting head 31. The driver 32 is an oil pressure device, but not limiting. The driver 32 is disposed on and supported by a column 34 of the torque testing machine 10. The column 34 is disposed between the first and second seats 25 and 26. The column 34 is disposed behind the testing head 11 and the first connecting head 21 in a direction transverse to the direction of the first axis L1. The shaft of the driver 32 travels between two limiting members 35. The two limiting members 35 are arranged separately in a direction of travel of the shaft. The two limiting members 35 are disposed on a bracket 36. The bracket 36 connects to the driver 32. The bracket 36 is disposed on the driver 32.

When an object to be tested is driven by the first drive device 20, the first connecting head 11 is in a rotational motion about the first axis L1 and creates a torque transmitted to the testing head 11.

When an object to be tested is driven by the second drive device 30, the second connecting head 31 is in a motion tangential to the distance D and creates a torque transmitted to the testing head 11.

The torque testing machine 10 of the present invention can test various types of objects.

Figure 5:
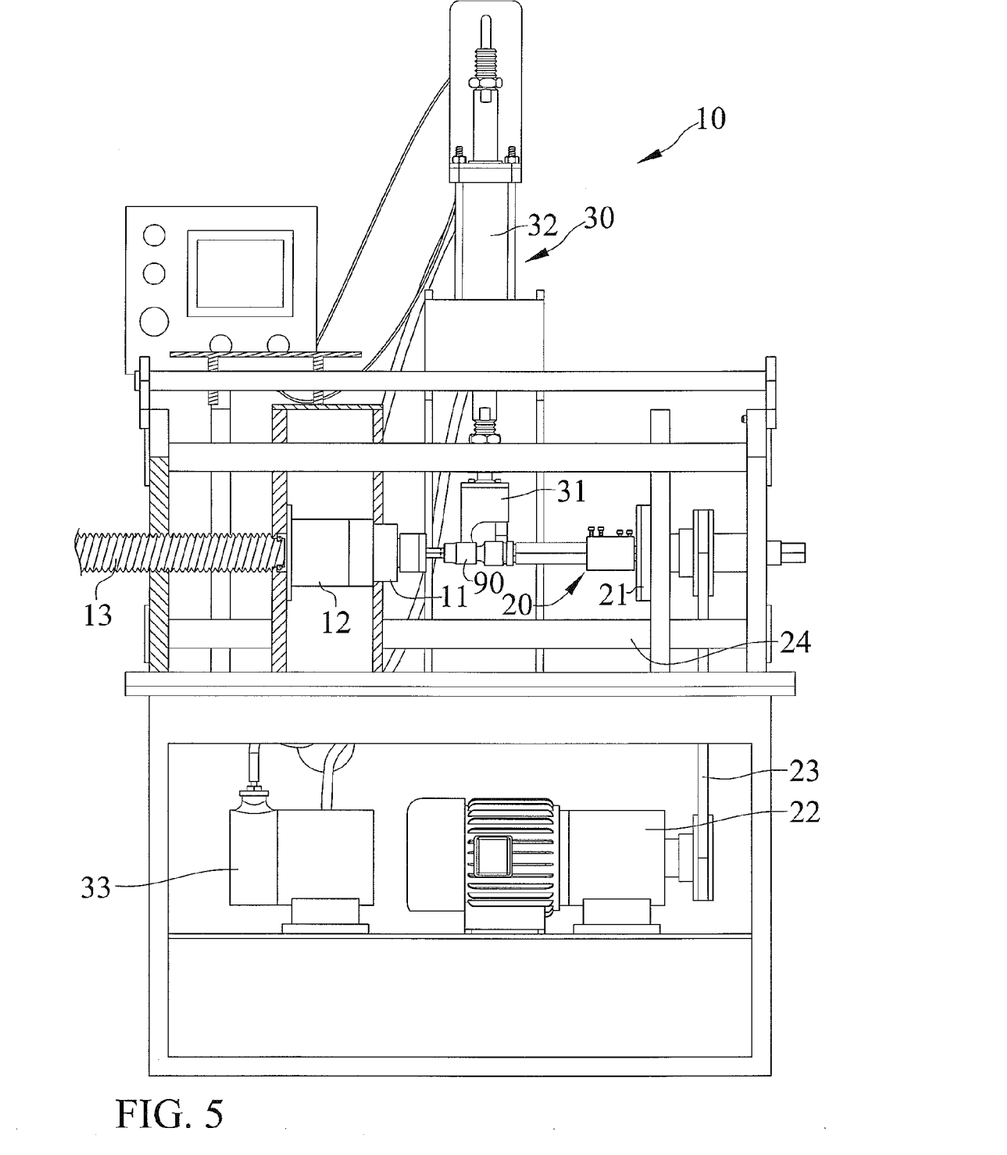
FIG. 5 is a cross-sectional view of the torque testing machine of the present invention and an object to be tested by the torque testing machine.

A first object 90 to be tested is a socket joint. The first object 90 under a torque test by the torque testing machine 10 of the present invention includes an end securing to the testing head 11 and another end securing to the connecting head 21 of the first drive device 20.

Figure 6:
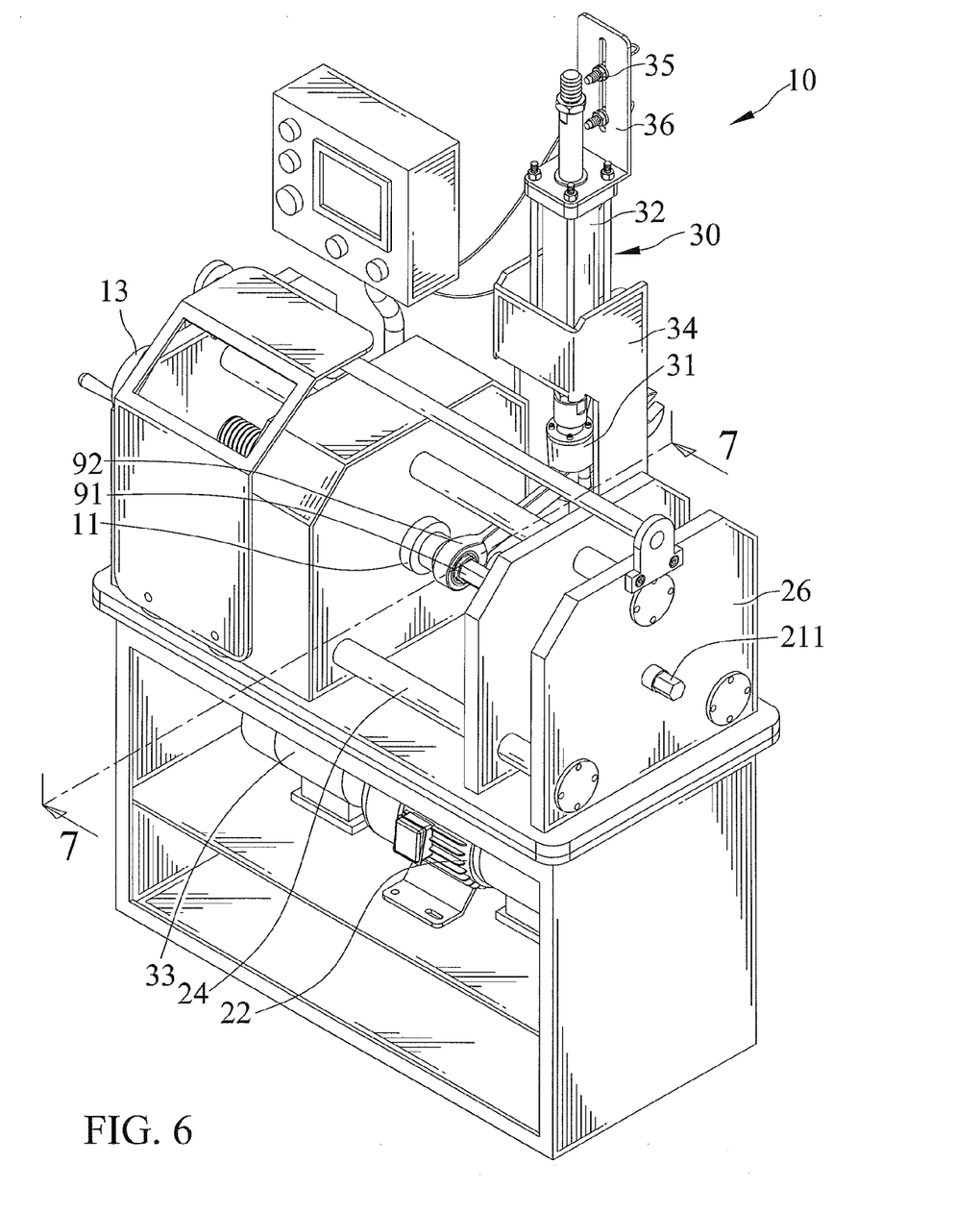
FIG. 6 is a perspective view of the torque testing machine of the present invention and another object to be tested by the torque testing machine.
Figure 7:
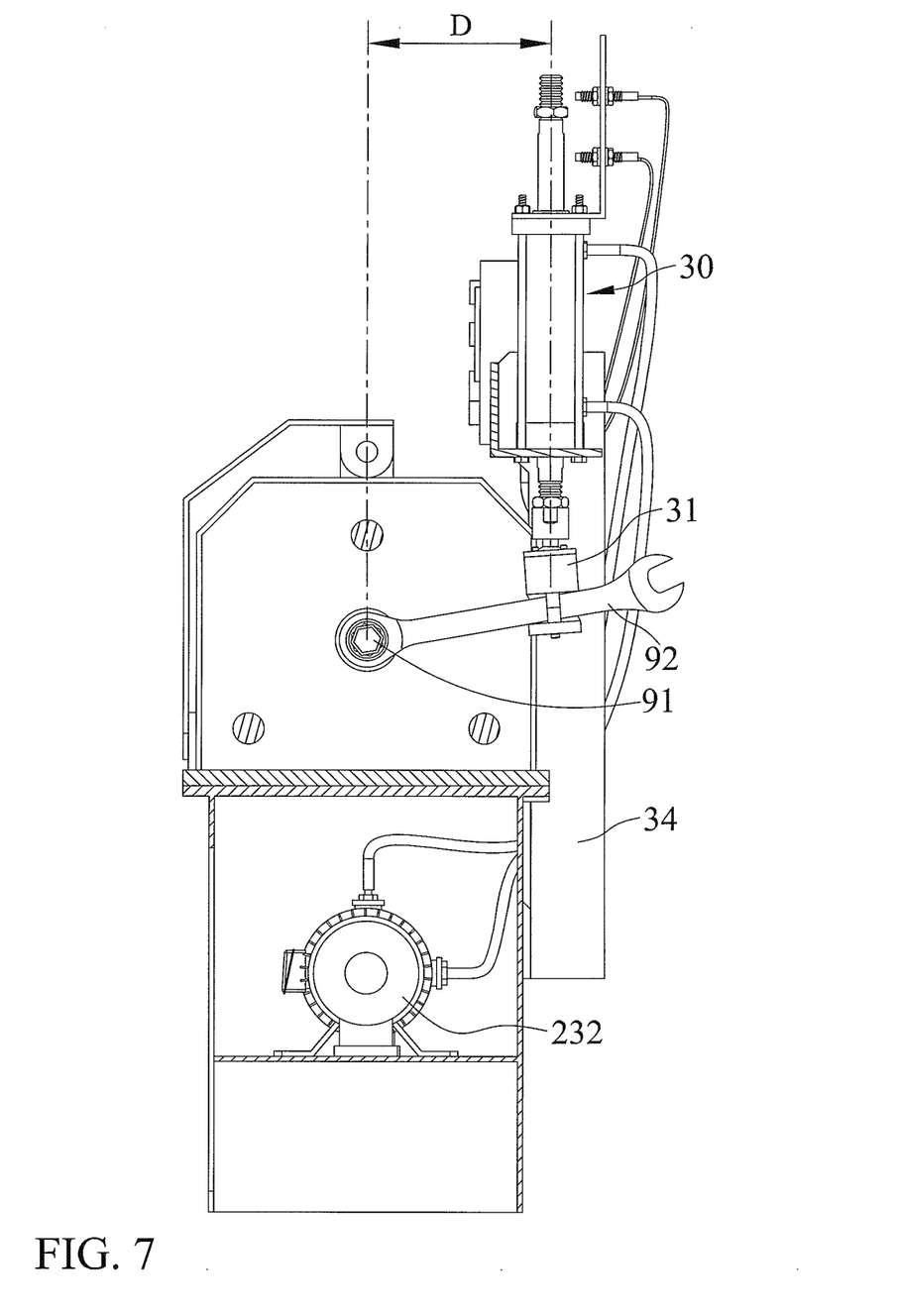
FIG. 7 is a cross-sectional view taken along line 7-7 of FIG. 6
Figure 8:
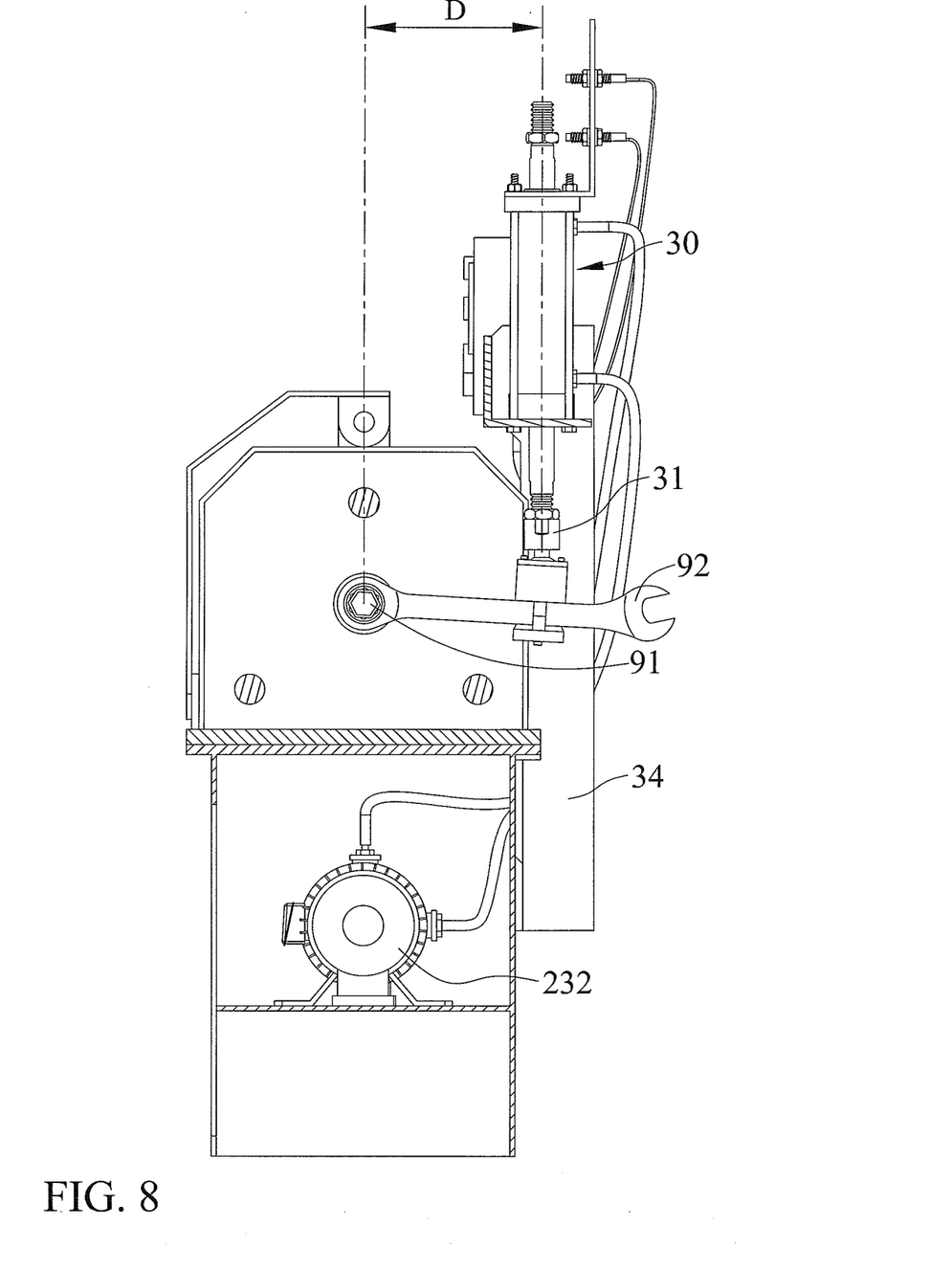
FIG. 8 is a cross-sectional view of the object to be tested shown in FIG. 7 under a torque test.

A second object 92 to be tested is a box wrench. A rod 91 is inserted through a compartment in a box end of the box wrench. The compartment of the box end of the box wrench is known for engaging with an object to be driven by the box wrench. In this embodiment, the compartment of the box end of the box wrench receives a rod 91 and includes the rod 91 inserting therethrough. The rod 91 includes an end securing to the testing head 11 and another end securing to the first connecting head 21 of the first drive device 20, respectively. The rod 91 is a hexagonal rod, which includes an outer periphery of a hexagonal shape. The rod 91 releasably secures to the testing head 11 and the first connecting head 21 for transmitting a torque the second object 92 to be tested withstands to the testing head 11.

Figure 9:
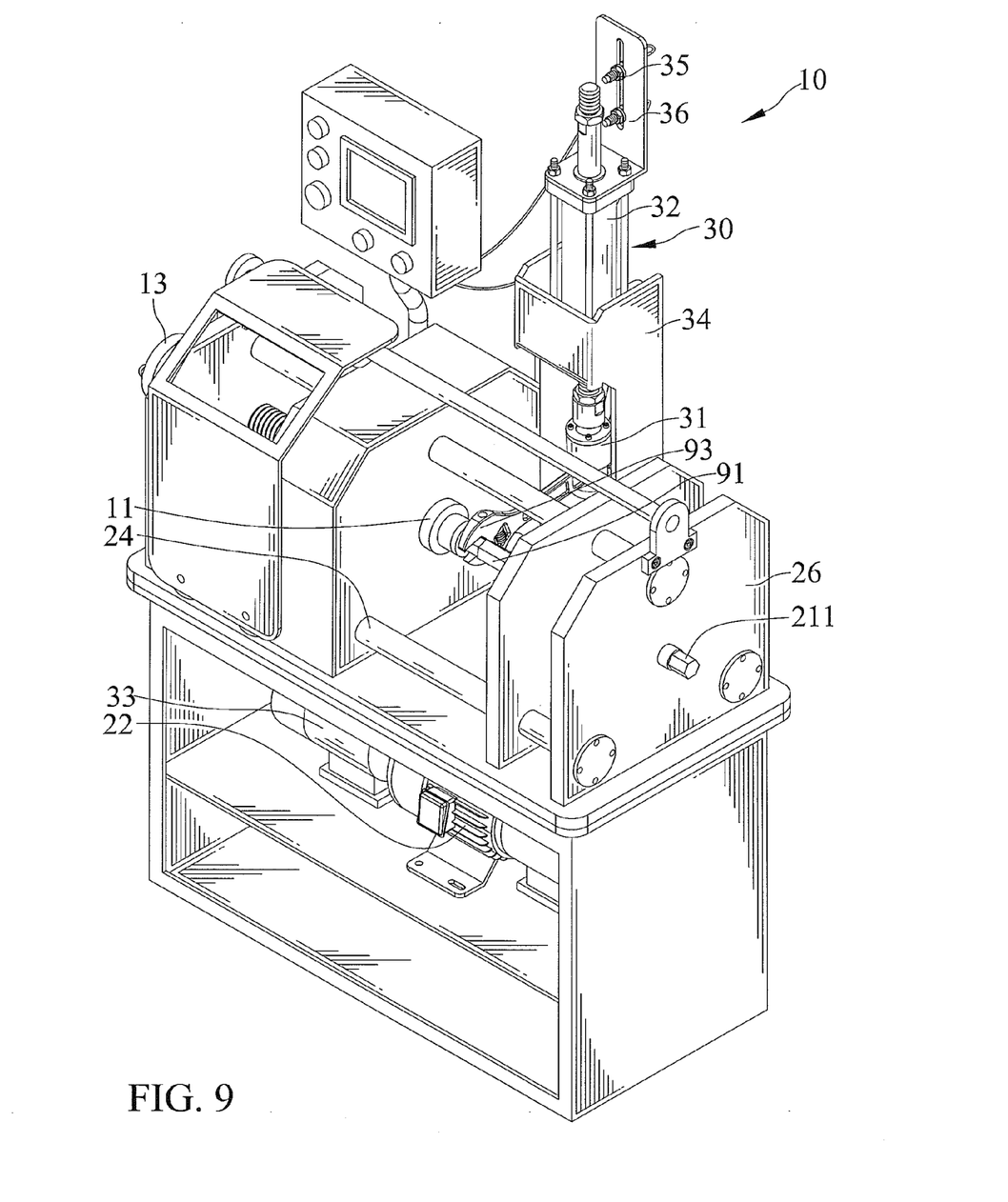
FIG. 9 is a perspective view of the torque testing machine of the present invention and another object to be tested by the torque testing machine.
Figure 10:
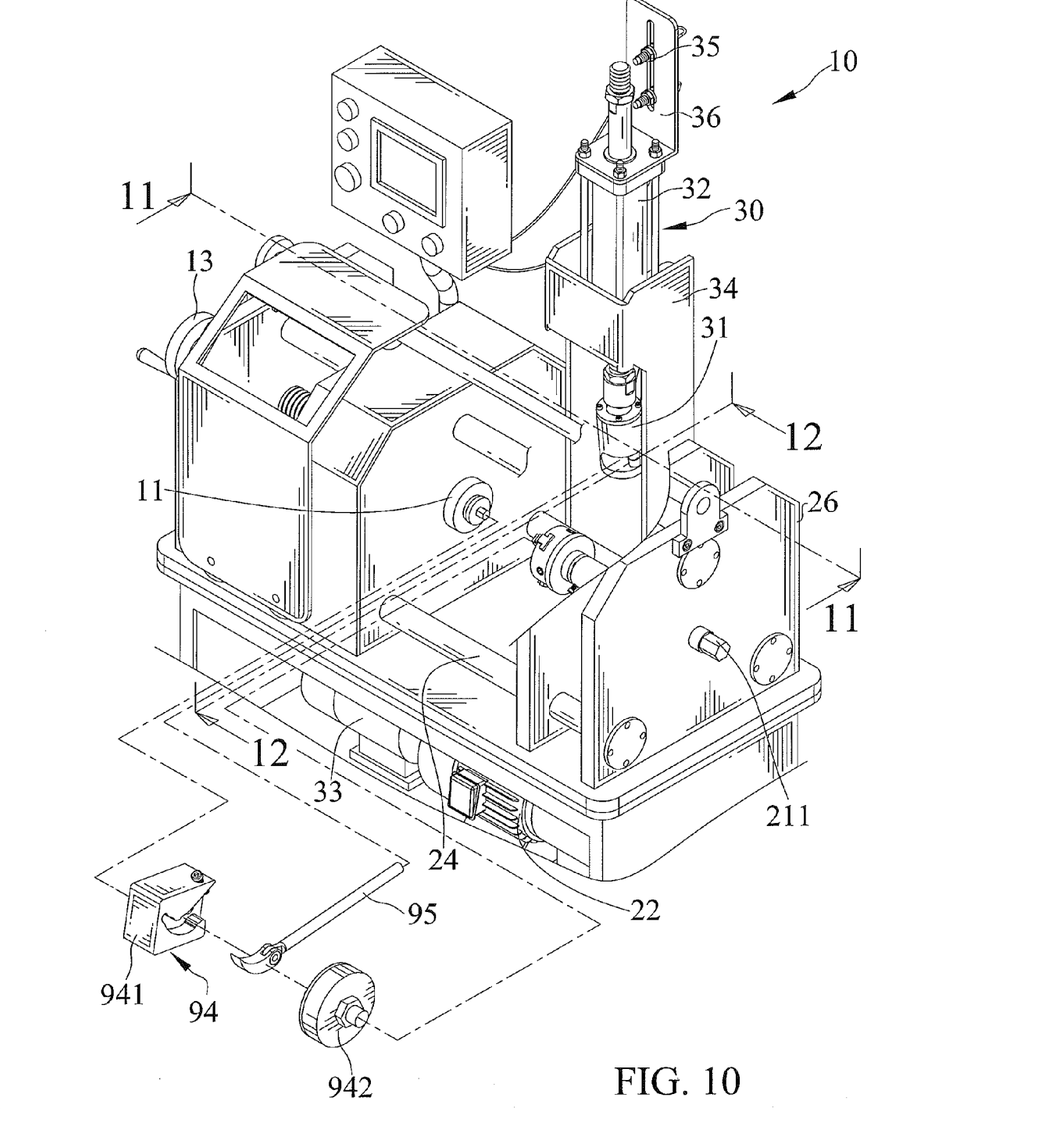
FIG. 10 is an exploded perspective view of the torque testing machine of the present invention and another object to be tested by the torque testing machine.
Figure 11:
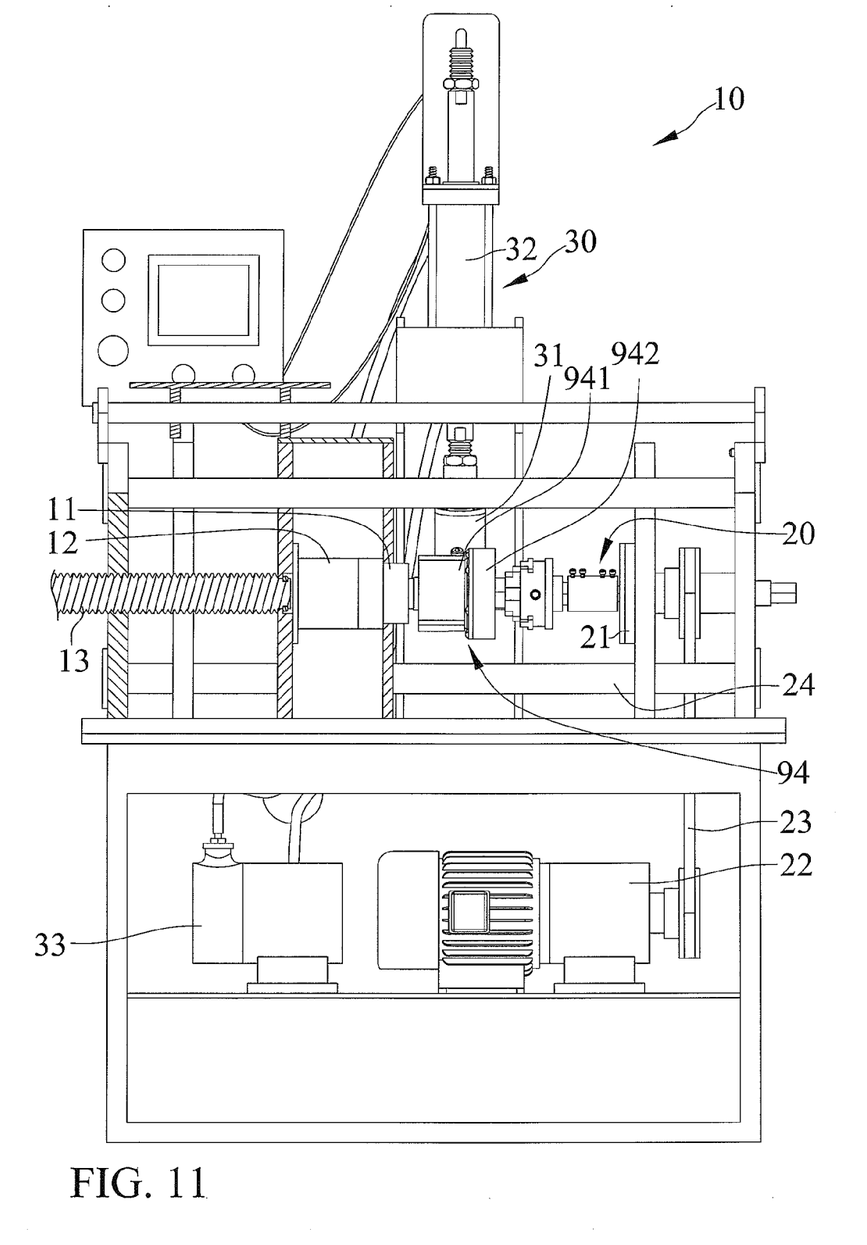
FIG. 11 is a cross-sectional view taken along line 11-11 of FIG. 10.
Figure 12:
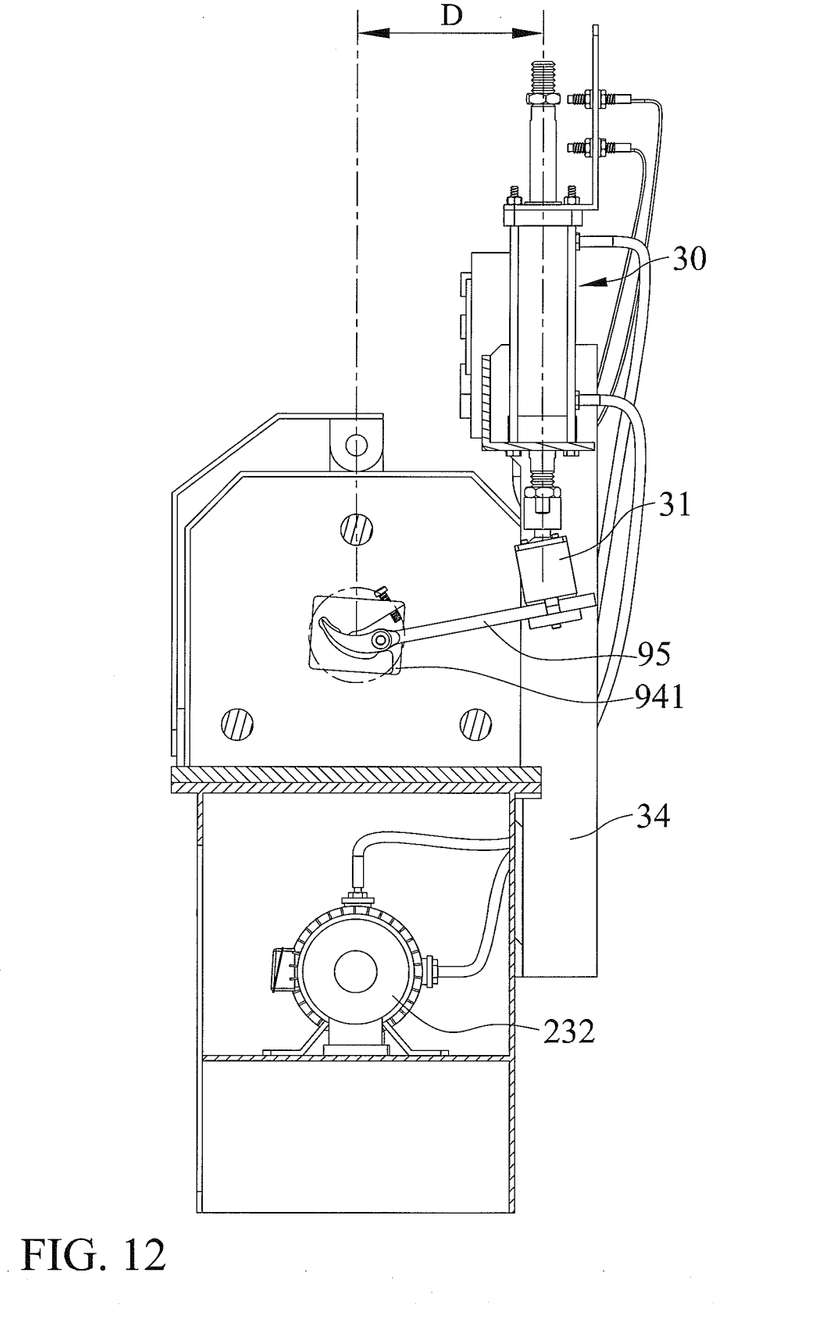
FIG. 12 is a cross-sectional view taken along line 12-12 of FIG. 10.
Figure 13:
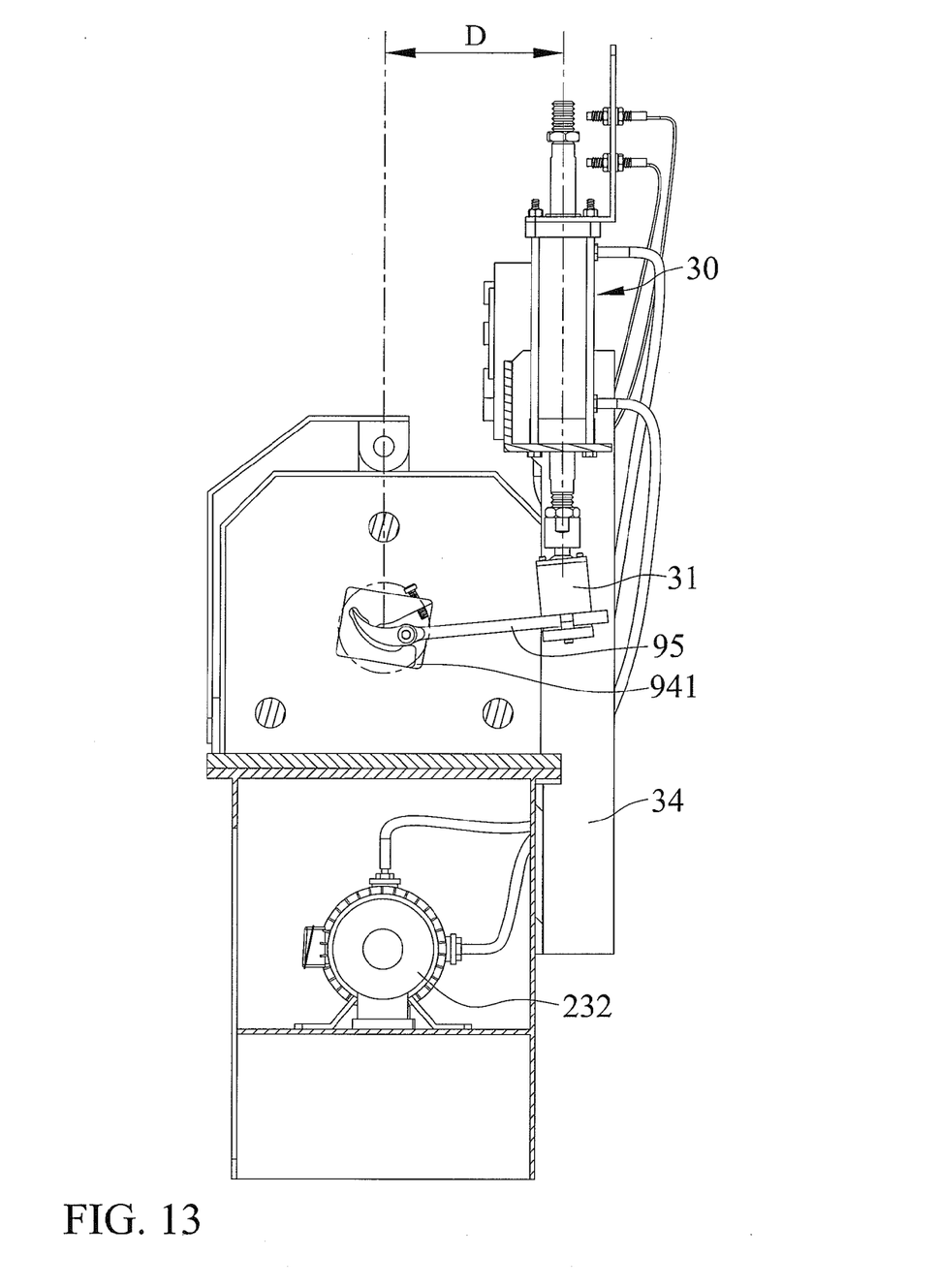
FIG. 13 is a cross-sectional view of the object to be tested shown in FIG. 12 under a torque test.

A third object 93 to be tested is a type of an open-end wrench. The third object 93 includes an open end with two jaws. In the embodiment, the two jaws have various relative positions. The third object 93 has an end engaging with the rod 91. The rod 91 is held between the two jaws. The third object 93 has another end held by the second connecting head 31. The rod 91 releasably secures to the testing head 11 and the first connecting head 21 for transmitting a torque the third object 93 to be tested withstands to the testing head 11.

A fourth object 95 to be tested is a pry bar. A mold 94 releasably secures to the testing head 11 and the first connecting head 21 for transmitting a torque the fourth object to be tested withstand to the test head 11. The mold 94 includes a first mold member 941 including a side with a recess. The mold 94 includes a second mold member 942 releasably securing to the side of the first mold member 941. An end of the fourth object 95 is received and retained in the recess. Another end of the forth object 95 is held by the second connecting head 31.

In view of the forgoing, the torque testing machine 10 includes at least two drive devices 20 and 30 being cooperative with the testing head 11. When an object to be tested is driven by the first drive device 20, the first connecting head 11 is in a rotational motion about the first axis L1 and creates a torque transmitted to the testing head 11. When an object to be tested is driven by the second drive device 30, the second connecting head 31 is in a motion tangential to the distance D and creates a torque transmitted to the testing head 11.

The foregoing is merely illustrative of the principles of this invention and various modifications can be made by those skilled in the art without departing from the scope and spirit of the invention.

What is claimed is:

1. A torque testing machine (10) comprising:
   a testing head (11) and a calculating device (22) connecting to the testing head to calculate a torque transmitted to the testing head;
   a first drive device (20) including a first connecting head (21) being cooperative with the testing head, with the first connecting head and the testing head opposing to each other, and with the first connecting head being rotatable about a first axis (L1); and
   a second drive device (30) including a second connecting head (31) being cooperative with the testing head, with the second connecting head offsetting a distance (D) from the first axis and movable tangentially to the distance;
   wherein when a first object to be tested is driven by the first drive device, the first connecting head is in a rotational motion about the first axis and creates a first torque transmitted to the testing head; and
   wherein when a second object to be tested is driven by the second drive device, the second connecting head is in a motion tangential to the distance and creates a second torque transmitted to the testing head.

2. The torque testing machine (10) as claimed in claim 1, wherein the testing head (11) is movable to various positions in a direction of a second axis (L2).

3. The torque testing machine (10) as claimed in claim 2, wherein the first and second axes (L1, L2) are aligned with each other.

4. The torque testing machine (10) as claimed in claim 1, wherein the first connecting head (21) includes a control input (211) extending therefrom and rotating therewith, and wherein the control input is operatively rotatable to cause the first connecting head in a rotational motion.

5. The torque testing machine (10) as claimed in claim 1 further including a first power source (22) to drive a first transmission mechanism to turn the first connecting head (21) and a second power source (33) to drive a second transmission mechanism to move the second connecting head (31) respectively, with the first drive transmission mechanism interconnecting the first power source and the first connecting head and the second transmission mechanism interconnecting the second power source and the second connecting head respectively.

6. The torque testing machine (10) as claimed in claim 5, wherein the second connecting head (31) is reciprocally movable, and wherein the second transmission mechanism includes a driver (32) with a shaft being reciprocally movable and connecting to the second connecting head.

7. The torque testing machine (10) as claimed in claim 6, wherein the driver (32) is disposed on and supported by a column (34) of the torque testing machine (10), and wherein the column is disposed behind the testing head (11) and the first connecting head (21) in a direction transverse to the direction of the first axis (L1).

8. The torque testing machine (10) as claimed in claim 6 further comprising two limiting members (35), and shaft of the driver (32) travels between the two limiting members, and wherein the two limiting members are arranged separately in a direction of travel of the shaft.

9. The torque testing machine (10) as claimed in claim 1 further comprising a rod (91) releasably securing to the testing head (11) and the first connecting head (21) for transmitting the second torque the second object to be tested withstands to the testing head (11).

10. The torque testing machine (10) as claimed in claim 1 further comprising a mold (94) releasably securing to the testing head (11) and the first connecting head (21) for transmitting the second torque the second object to be tested withstand to the test head (11).

11. The torque testing machine (10) as claimed in claim 10, wherein the mold (94) includes a first mold member (941) including a side with a recess, and wherein the mold includes a second mold member (942) releasably securing to the side of the first mold member.

12. The torque testing machine (10) as claimed in claim 9 further including a first power source (22) to drive a first transmission mechanism to turn the first connecting head (21) and a second power source (33) to drive a second transmission mechanism to move the second connecting head (31) respectively, with the first drive transmission mechanism interconnecting the first power source and the first connecting head and the second transmission mechanism interconnecting the second power source and the second connecting head respectively.

13. The torque testing machine (10) as claimed in claim 12, wherein the second connecting head (31) is reciprocally movable, and wherein the second transmission mechanism includes a driver (32) with a shaft being reciprocally movable and connecting to the second connecting head.

14. The torque testing machine (10) as claimed in claim 10 further including a first power source (22) to drive a first transmission mechanism to turn the first connecting head (21) and a second power source (33) to drive a second transmission mechanism to move the second connecting head (31) respectively, with the first drive transmission mechanism interconnecting the first power source and the first connecting head and the second transmission mechanism interconnecting the second power source and the second connecting head respectively.

15. The torque testing machine (10) as claimed in claim 14, wherein the second connecting head (31) is reciprocally movable, and wherein the second transmission mechanism includes a driver (32) with a shaft being reciprocally movable and connecting to the second connecting head.

* * * * *